(12) United States Patent
Dallerup Rasmussen et al.

(10) Patent No.: US 12,216,118 B2
(45) Date of Patent: Feb. 4, 2025

(54) SYSTEM FOR DETERMINING VALIDITY OF A LATERAL FLOW TEST RESULT

(71) Applicant: DELAVAL HOLDING AB, Tumba (SE)

(72) Inventors: Claus Dallerup Rasmussen, Tumba (SE); Jonas Trier Hald, Tumba (SE)

(73) Assignee: DeLaval Holding AB, Tumba (SE)

( * ) Notice: Subject to any disclaimer, the term of this patent is extended or adjusted under 35 U.S.C. 154(b) by 645 days.

(21) Appl. No.: 17/619,110

(22) PCT Filed: Jun. 9, 2020

(86) PCT No.: PCT/SE2020/050586
§ 371 (c)(1),
(2) Date: Dec. 14, 2021

(87) PCT Pub. No.: WO2020/251460
PCT Pub. Date: Dec. 17, 2020

(65) Prior Publication Data
US 2022/0276242 A1    Sep. 1, 2022

(30) Foreign Application Priority Data
Jun. 14, 2019  (SE) .................................. 1950719-3

(51) Int. Cl.
*G01N 33/543* (2006.01)
*G01N 33/53* (2006.01)
*G01N 33/74* (2006.01)

(52) U.S. Cl.
CPC ... *G01N 33/54388* (2021.08); *G01N 33/5302* (2013.01); *G01N 33/74* (2013.01)

(58) Field of Classification Search
CPC ........... G01N 21/8483; G01N 33/5302; G01N 33/54388; G01N 33/558; G01N 33/74; G01N 33/743; G01N 33/04
See application file for complete search history.

(56) References Cited

U.S. PATENT DOCUMENTS 10,175,162 B2   1/2019  Jia et al.
2002/0168781 A1  11/2002  Seong
(Continued)

FOREIGN PATENT DOCUMENTS

CN   1379246 A   11/2002
CN   102033109 A   4/2011
(Continued)

OTHER PUBLICATIONS

Office Action, issued in Japanese Patent Application No. 2021-573792 dated Apr. 10, 2024.
(Continued)

*Primary Examiner* — Jennifer Wecker
*Assistant Examiner* — Jonathan Bortoli
(74) *Attorney, Agent, or Firm* — NIXON & VANDERHYE (57) ABSTRACT

A system, a sensor and a control unit for determining validity of a result of a lateral flow test, whereby a lateral flow stick that has a sample pad, a conjugate pad having antibody treated gold particles, and a porous membrane for receiving a capillary flow of a milk sample. The porous membrane has a test line treated with a progesterone reference which binds antibody treated gold particles of the milk sample and thereby brings the test line to change colour tint when exposed for milk comprising a progesterone level lower than a threshold limit, and a control line treated with an antibody reference which binds antibody, and thereby brings the control line to change colour tint when exposed for milk comprising antibody treated gold particles.

9 Claims, 4 Drawing Sheets

(56) References Cited

U.S. PATENT DOCUMENTS

| | | |
|---|---|---|
| 2003/0124618 A1 | 7/2003 | Chen et al. |
| 2005/0003522 A1 | 1/2005 | Carlsen et al. |
| 2011/0072885 A1 | 3/2011 | Inana |
| 2012/0021531 A1 | 1/2012 | Ellis |
| 2012/0072125 A1 | 3/2012 | Sharrock |
| 2012/0282636 A1* | 11/2012 | Altschul ............. G01N 33/525 422/69 |
| 2016/0225165 A1 | 8/2016 | Russell et al. |
| 2016/0370366 A1 | 12/2016 | Fleming et al. |
| 2019/0204334 A1* | 7/2019 | McCarthy ............ G01N 33/743 |

FOREIGN PATENT DOCUMENTS

| | | |
|---|---|---|
| CN | 102099678 A | 6/2011 |
| CN | 102105795 A | 6/2011 |
| EP | 1 248 111 | 10/2002 |
| EP | 2309256 A2 | 4/2011 |
| JP | 2002328127 A | 11/2002 |
| JP | 2011075366 A | 4/2011 |
| WO | 2018/011796 | 1/2018 |
| WO | 2018/236271 | 12/2018 |
| WO | 2019/112944 | 6/2019 |
| WO | 2019/133920 | 7/2019 |

OTHER PUBLICATIONS

Chuang Xu, et al., "Development of a Competitive Lateral Flow Immunoassay for Progesterone in Dairy Cows' Milk", Med. Weter., vol. 72, No. 8, 2016, pp. 494-497 (4 pages).

Search Report for SE Application No. 1950719-3 dated Feb. 25, 2020, 3 pages.

International Search Report for PCT/SE2020/050586 dated Sep. 17, 2020, 5 pages.

Written Opinion of the ISA for PCT/SE2020/050586 dated Sep. 17, 2020, 7 pages.

Office Action, issued in Chinese Patent Application No. 202080042276.X dated Aug. 24, 2024.

* cited by examiner

SYSTEM FOR DETERMINING VALIDITY OF A LATERAL FLOW TEST RESULT

TECHNICAL FIELD

This document discloses a system. More particularly, a system is described, for determining validity of a result of a lateral flow test, performed on a lateral flow stick arranged to indicate progesterone in a milk sample of an animal.

BACKGROUND

On an animal farm, it is important to keep the animals healthy in order to enhance milk/meat production. On a dairy farm, for example, it is very important to inseminate animals at an optimal moment in order to successfully fertilise the cow. It is important to find the right moment to inseminate each individual animal in the farm, for efficiency reasons. In case the animal is not successfully inseminated, milk production is affected.

Several biomarker measurements may be made on the animal, such as e.g. measuring levels of progesterone, LDH (Lactate Dehydrogenase), BHB (Beta-Hydroxybutyrat) and urea. Thereby important information concerning e.g. heat detection and/or pregnancy of the individual animal may be made (based on measured progesterone level), as well as mastitis (based on LDH) and ketosis (based on BHB). Also, the energy balance may be estimated (based on urea).

A milk analysis apparatus/service module may be arranged to cooperate with a milk extracting arrangement, for regularly analysing milk samples of the animals, e.g. at or around the moment of a milking session. The milk analysis apparatus/service module may extract a milk sample and provide it on a lateral flow stick/lateral flow test strip/dry stick or similar. The milk may be diluted with a diluent, which also may be used to rinse the tubings between test sessions. The diluent may be provided in a liquid container.

The lateral flow sticks may be maintained in a cassette, for example on a tape in the cassette as disclosed in document WO 2018236271. Thereby milk analysis units may be easily administrated at the farm by forwarding one lateral flow stick at the time. One lateral flow stick may typically be used for each test sample. The cassette may comprise a large amount of lateral flow sticks, yet the cassette with the lateral flow sticks have to be exchanged for a new one when all the lateral flow sticks have been consumed.

Thereby, a farmer/operator is provided with important information concerning each individual animal. The biomarker such as progesterone may be measured of all individual animals at the farm with a high degree of automation.

However, a problem that may occur is that it is impossible for the farmer to determine whether the result of the lateral flow test is valid. Lateral flow sticks may be affected by moisture and/or storage in high temperature, for example. In case the lateral flow stick is defect for some reason, it may be impossible to make a positive detection of low progesterone in the milk sample, resulting in an undetected heat of animals.

It would for these reasons be advantageous to find a way to ascertain that lateral flow sticks are in good condition and/or that a lateral flow test performed on the lateral flow stick are valid and reliable, preferably without putting an additional work load on the farmer for determining the validity.

SUMMARY

It is therefore an object of this invention to solve at least some of the above problems and facilitate for a farmer to indicate presence of progesterone in a milk sample of an animal in a lateral flow test, and to determine validity of the result of the lateral flow test.

According to a first aspect of the invention, this objective is achieved by a system for determining validity of a result of a lateral flow test. The system comprises a lateral flow stick arranged to indicate progesterone in a milk sample of an animal by a lateral flow test. The lateral flow stick comprises a sample pad, configured to receive the milk sample. Also, the lateral flow stick comprises a conjugate pad comprising antibody treated gold particles, which are dispersed into the milk sample when the milk sample is absorbed from the sample pad. In addition, the lateral flow stick also comprises a porous membrane for receiving a capillary flow of the milk sample, from the conjugate pad. The porous membrane comprises a test line treated with a progesterone reference which binds antibody treated gold particles of the milk sample and thereby brings the test line to change colour tint when exposed for milk comprising a progesterone level lower than a threshold limit. The porous membrane also comprises a control line treated with an antibody reference which binds antibody treated gold particles of the milk sample regardless of the progesterone level in the milk, and thereby brings the control line to change colour tint when exposed for milk comprising antibody treated gold particles. The system in addition comprises a sensor configured to capture an image of the control line of the lateral flow stick when a milk sample has been absorbed by a porous membrane comprising the test line and the control line. Furthermore, the system also comprises a control unit. The control unit is configured to obtain a reference colour tint of the control line. The control unit is also configured to determine a current colour tint of the control line, based on the image captured by the sensor during the ongoing lateral flow test. In addition, the control unit is configured to compare the reference colour tint of the control line with the current colour tint of the control line. The control unit, furthermore, is configured to indicate validity of the lateral flow test on the lateral flow stick, based on the made comparison.

The system is intended to operate autonomously in an agricultural environment such as a barn. The temperature may become very high in a barn, e.g. in summertime and temperature regulating arrangements in the barn (if any) may malfunction or be insufficient. High temperature, or otherwise inappropriate storage of the lateral flow sticks may cause the antibody treated gold particles of the conjugate pad to burn into the cellulose. The milk sample will then not release enough gold particles to get a reliable progesterone measurement in the test line. By obtaining a reference colour tint of the control line and compare the current colour tint of the control line with the reference colour tint, ageing or deteriorating of the lateral flow sticks may be detected at an early stage. Hereby the reliability of the lateral flow test based on the lateral flow sticks is increased.

In a first possible implementation of the system according to the first aspect, the control unit may be configured to generate an alert when a colour tint difference exceeding a threshold limit is detected between the reference colour tint of the control line and the current colour tint of the control line.

The farmer may thereby be alerted to change the lateral flow sticks before they have deteriorated so much that the result of the lateral flow test is affected. The farmer is released from the stress of continuously checking validity of the lateral flow sticks.

In a second possible implementation of the system according to the first aspect, or according to the first implementation thereof, the control unit may be configured to disable usage of the lateral flow stick comprising the control line, upon detection of the colour tint difference exceeding a threshold limit is detected between the reference colour tint of the control line and the current colour tint of the control line.

By disabling usage of the lateral flow stick when the colour tint difference exceeding the threshold limit is detected on the control line, it is ascertained that lateral flow tests are not believed to be valid when the lateral flow stick is aged/deteriorated leading to higher validity and trust of the biomarker test.

In a third possible implementation of the system according to the first aspect, or according to any previously disclosed implementation thereof, the system may comprise a first wireless communication device. In those embodiments, the lateral flow stick may be maintained in a cassette comprising a second wireless communication device for wireless communication with the first wireless communication device, and a memory device. Further, the comprised control unit may be configured to transmit a blocking sign prohibiting further usage of the cassette, via the first wireless communication device and the second wireless communication device, for storage in the memory device of the cassette, when the colour tint difference is detected.

By storing the blocking sign in the memory of the cassette, it becomes impossible to use the lateral flow sticks/cassette in any other apparatus, also when other apparatus is not able to indicate validity of the lateral flow test.

In a fourth possible implementation of the system according to the first aspect, or according to any previously disclosed implementation thereof, the reference colour tint of the control line may be obtained by extraction of a prestored reference colour tint sample from a memory device.

By determine and store the colour tint of the control line during a relatively early test such as e.g. on the first lateral flow stick on a cassette used for the first time, and then use it as a reference colour tint for a subsequent test, a reliable reference colour tint is obtained, leading to that also a very small deterioration of chemicals on the lateral flow stick over time is detectable and could be determined.

In a fifth possible implementation of the system according to the first aspect, or according to any previously disclosed implementation thereof, the reference colour tint of the control line may be obtained by extraction of a representation, such as a value or an image representing the control line of the lateral flow stick, captured by the sensor during a previous milk analysis session, from a memory device.

By storing and extracting the reference colour tint to/from the memory device, it is assured that the comparison of control line colour tint is made with the correct reference colour tint, enhancing reliability of the lateral flow test and the lateral flow sticks.

In a sixth possible implementation of the system according to the first aspect, or according to any previously disclosed implementation thereof, the reference colour tint of the control line may be obtained by capturing an image of a reference line of the lateral flow stick.

By applying a reference line on the lateral flow stick during the manufacturing of the lateral flow stick, it becomes possible to capture an image of the reference line, the control line and/or the test line and compare the respective colour tint. It is hereby not required to determine reference colour tint, store the reference colour tint in a memory and then retrieve the reference colour tint from the memory for making the comparison between the reference colour tint and the control line. Hereby, a speedy and reliable determination may be made, whether the lateral flow stick/test is valid. Further, no memory is required, which saves resources and eliminates any possible error during memory reading.

In a seventh possible implementation of the system according to the first aspect, or according to any previously disclosed implementation thereof, the lateral flow stick is configured to expose at least a part of the control line on the porous membrane for direct visual contact with the sensor. The sensor may be arranged to have direct visual contact with at least a part of the control line on the porous membrane of the lateral flow stick when capturing the image thereof, in order to avoid optical distortion.

By peeling off, or otherwise avoid having a plastic cover or similar covering the porous membrane, it is assured that the captured image by the sensor is not distorted or otherwise becomes difficult to distinguish.

In an eighth possible implementation of the system according to the first aspect, or according to any previously disclosed implementation thereof, the control line of the lateral flow stick may be arranged more distant from the sample pad than the test line.

By placing the control line downstream in relation to the test line, it is assured that the gold particle has passed the region of the sample pad comprising the test line in case the control line has changed colour tint. Reliability of the lateral flow test is further increased.

Thanks to the described aspects, by determining validity of the result of the lateral flow test, the manual intervention, maintenance and work intensity of the farmer is minimised or at least reduced.

Other advantages and additional novel features will become apparent from the subsequent detailed description.

FIGURES

Embodiments of the invention will now be described in further detail with reference to the accompanying figures, in which.

DETAILED DESCRIPTION

Embodiments of the invention described herein are defined as a system, which may be put into practice in the embodiments described below. These embodiments may, however, be exemplified and realised in many different forms and are not to be limited to the examples set forth herein; rather, these illustrative examples of embodiments are provided so that this disclosure will be thorough and complete.

Still other objects and features may become apparent from the following detailed description, considered in conjunction with the accompanying drawings. It is to be understood, however, that the drawings are designed solely for purposes of illustration and not as a definition of the limits of the herein disclosed embodiments, for which reference is to be made to the appended claims. Further, the drawings are not necessarily drawn to scale and, unless otherwise indicated, they are merely intended to conceptually illustrate the structures and procedures described herein.

Figure 1:
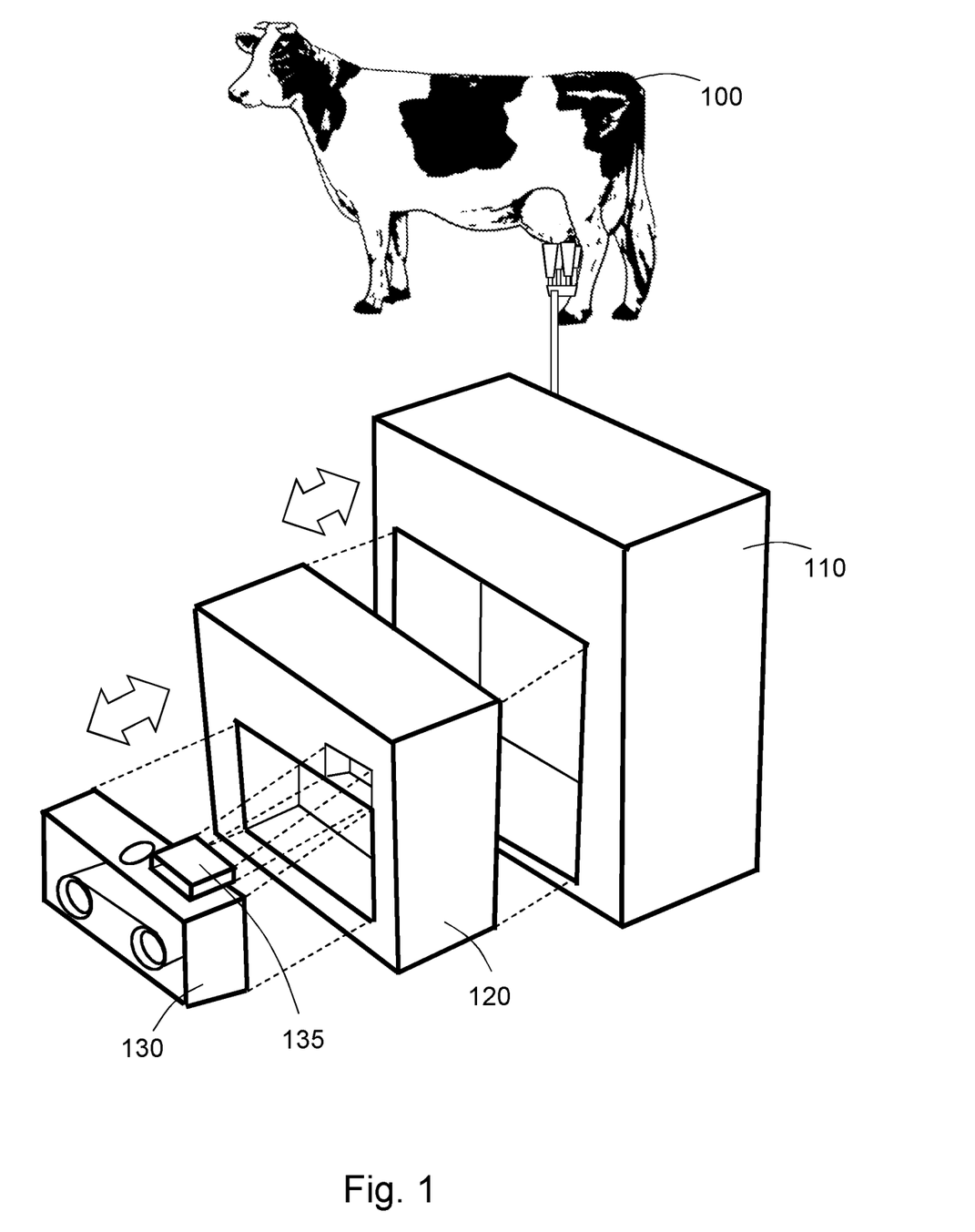
FIG. 1 illustrates an example of an arrangement for measuring a biomarker value of a milk sample of an animal.

FIG. 1 illustrates a scenario with an animal 100 which may be comprised in a herd of dairy animals at a dairy farm and a system 10 for determining validity of a result of a lateral flow test.

"Animal" may be any arbitrary type of domesticated female milk producing and/or meat producing mammal such as cow, goat, sheep, horse, camel, primate, dairy buffalo, donkey, yak, etc.

Milk of the animal 100 may be extracted by a milking equipment 110 such as e.g. a milking robot, rotary milking parlour or other milking arrangement for automatic or voluntary milking system and provided to a service module 120.

The service module 120 may be releasably inserted into the milking equipment 110 in some embodiments. Thus, there may be an interface between the milking equipment 110 and the service module 120 for providing milk and possibly electricity via the milking equipment 110 to the service module 120.

The service module 120 comprises various electronics and equipment such as a camera, one or several pumps, a tube element for attachment to the interface to the milking equipment 110, motors, a communication unit etc.

A cassette 130 may be detachably inserted into the service module 120. The cassette 130 comprises a tape with lateral flow sticks, or dry sticks as they also may be referred to as, configured to indicate a biomarker value of a milk sample of the animal 100. The cassette 130 may in some embodiments be configured to be detachably inserted in the service module 120 and held in place by a fastening means such as a snap lock, a magnet, a screw, etc., and a door of the service module 120 may be closed for enclosing the cassette 130 within the service module 120, thereby further fixating the cassette 130 in the position.

Thereby, a milk sample of the animal 100 may be extracted from the animal 100 by the milking equipment and provided via the service module 120 to one of the lateral flow sticks on the tape of the cassette 130. The lateral flow sticks may react on presence and/or amount of one or several biomarkers, e.g. by changing colours, colour tint or intensity of a colour/tint. The camera in the service module 120 may capture an image through an opening in the cassette 130. The captured image of the lateral flow sticks may then be analysed by a control unit, and based on the intensity of the colour, presence and/or quantity of the biomarker in the milk sample may be estimated.

The measured biomarker may be e.g. progesterone, glycoprotein, oestrogen and/or Gonadatropin-Releasing Hormones, or any other similar biomarker associated with reproduction of the animal 100, in different embodiments.

Progesterone is a hormone that regulates several physiological functions of the animal 100. Progesterone may prepare the uterus for pregnancy, maintain the pregnancy if fertilisation occurs, and inhibit the animal 100 from showing signs of standing oestrus and ovulating when pregnant. Progesterone levels, for example, may rise at the beginning of the pregnancy, and be kept ata high level throughout the pregnancy of the animal 100. Progesterone levels in milk samples may be used to monitor pregnancy, oestrous cycles (heat detection) and/or postpartum ovarian activity. For these reasons, progesterone levels of animals 100 at the farm is interesting for the farmer to detect and keep track of.

However, the measured biomarker may in some embodiments comprise LDH (Lactate Dehydrogenase), BHB (Beta-HydroxyButyrat), urea, and/or somatic cell count; or other biomarker related to status of the animal 100. In some embodiments, a plurality of the above enumerated biomarkers may be measured. Alternatively, in some embodiment, the farmer may subscribe to a cassette 130 comprising a certain lateral flow stick on the tape configured to measure a biomarker, or a set of biomarkers, as selected by the farmer; and/or different cassettes 130 comprising lateral flow sticks on the tape configured to measure different biomarkers, or sets of biomarkers, during different periods of time of the year.

In some embodiments, a dosing module may also be detachably inserted into the service module 120. The dosing module may comprise for example a needle, and/or one or several pumps. A diluent container with diluent may be external to the dosing module.

Figures 2A, 2B:
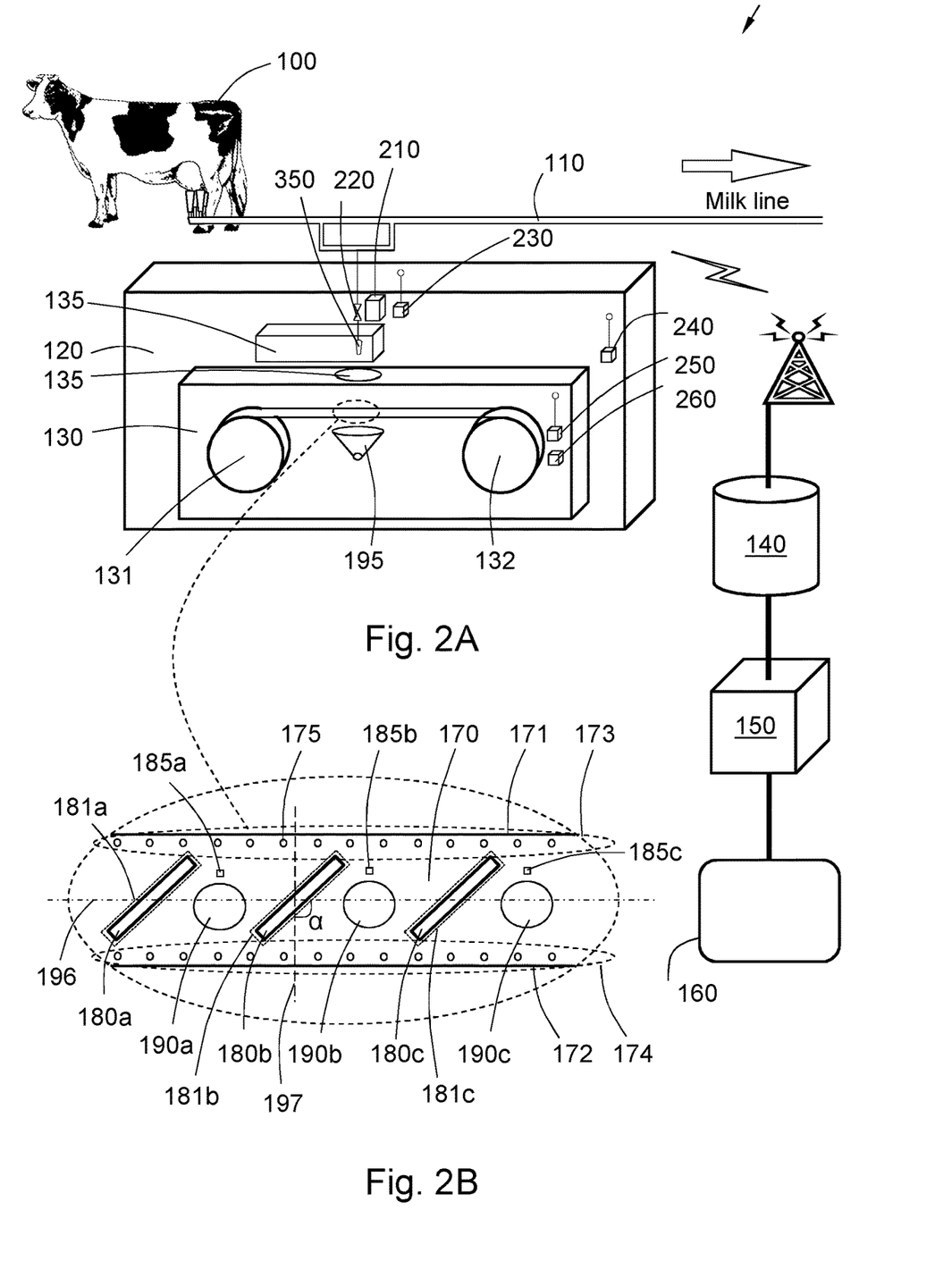
FIG. 2A illustrates a cassette inserted into a service module, according to an embodiment.
FIG. 2B illustrates a tape comprising lateral flow sticks, according to an embodiment.
Figure 3A:
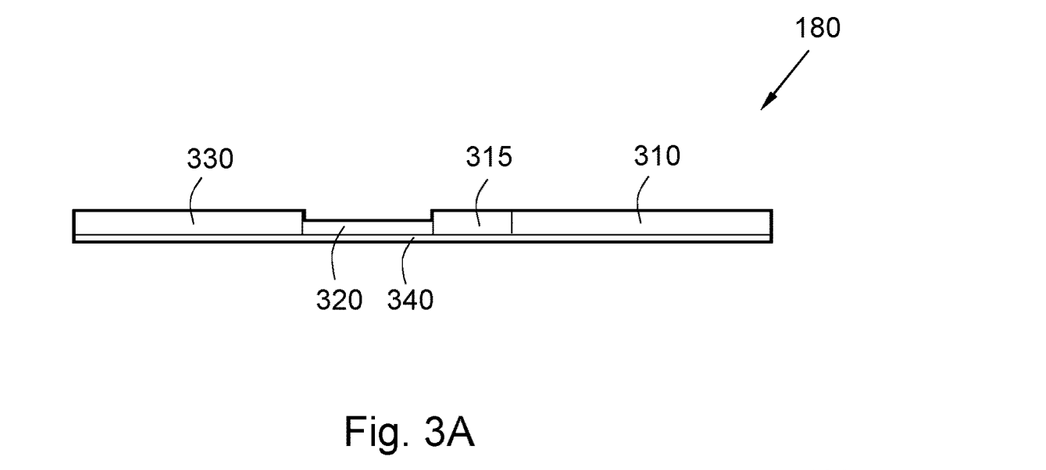
FIG. 3A illustrates a lateral flow stick, according to an embodiment.
Figure 3B:
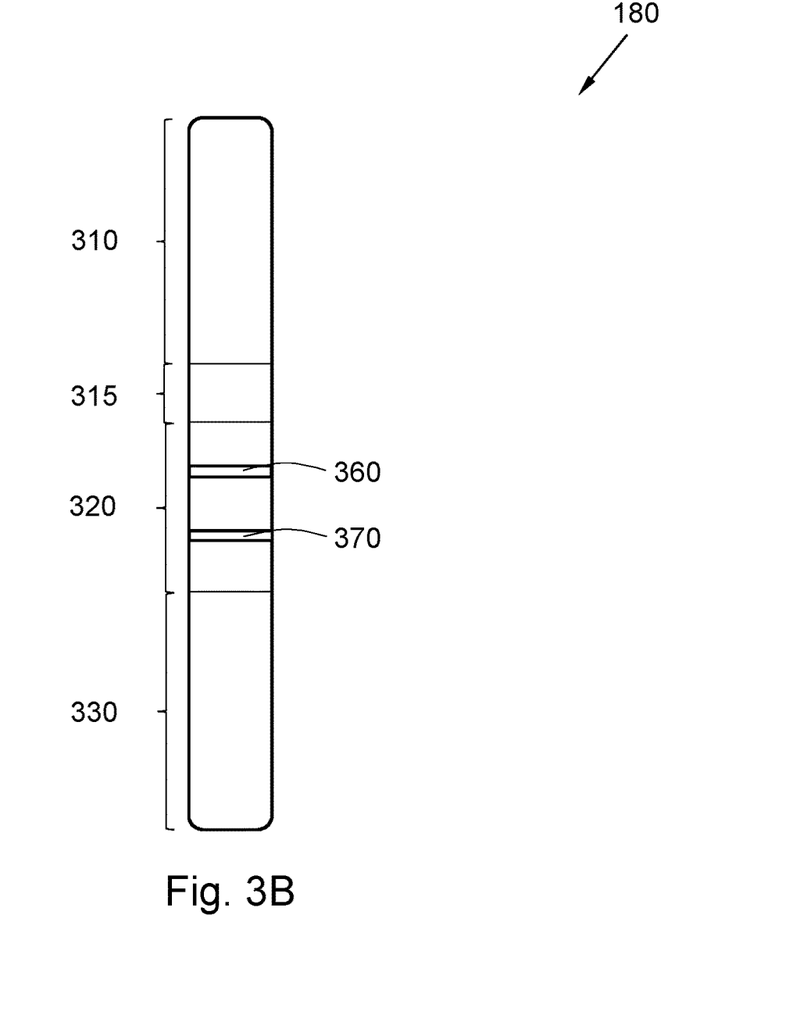
FIG. 3B illustrates a lateral flow stick, according to an embodiment.
Figure 4A:
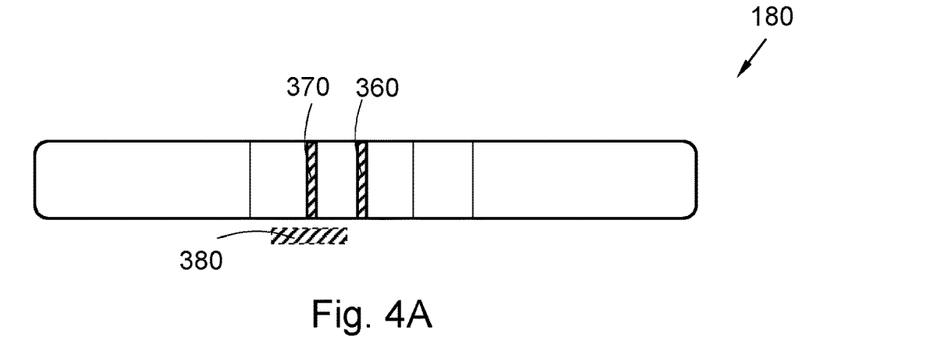
FIG. 4A illustrates a result of a lateral flow test on a lateral flow stick, according to an embodiment.
Figure 4B:
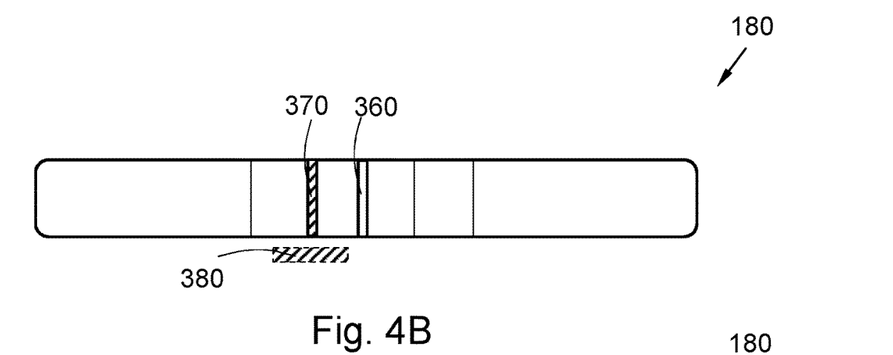
FIG. 4B illustrates a result of a lateral flow test on a lateral flow stick, according to an embodiment.
Figure 4C:
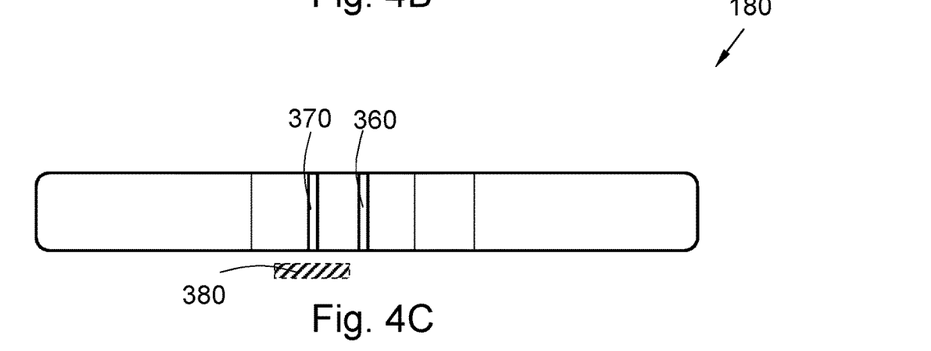
FIG. 4C illustrates a result of a lateral flow test on a lateral flow stick, according to an embodiment.

FIG. 1 and FIG. 2A depict general overviews of the provided solution, without going too much into details, in order for the reader to get a rough overview. Examples of details of the involved entities, in particular the cassette 130 and the tape, and how they interact with each other, and how the lateral flow sticks may be arranged are disclosed in FIG. 2B. Details of the lateral flow stick is depicted in FIG. 3A and FIG. 3B while FIGS. 4A, 4B and 4C illustrates examples of the results of lateral flow tests on a lateral flow stick.

FIG. 2A illustrates a scenario illustrating a service module 120, a cassette 130, and a dosing module, according to an embodiment, and a system 10. The service module 120 comprises electronics and equipment such as e.g. a sensor 210 for example a camera or video camera, a tube element 220 for attachment to the milking equipment, a motor, a communication unit 230, etc., to be used for determining a biometric value of a milk sample received from an animal 100. In some embodiments, the dosing module may comprise one or several pumps configured to act on the tube element 220 for advancing the milk sample through the tube element 220.

In the illustrated embodiment, the dosing module may comprise a needle 350 for applying the milk sample to a lateral flow stick 180a, 180b, 180c on a tape 170 in the cassette 130 through an opening in the cassette 130. The sensor 210 may then align the needle 350 with the lateral flow stick 180a, 180b, 180c on the tape 170 of the cassette 130.

The camera 210 of the service module 120 may capture an image of the lateral flow stick 180a, 180b, 180c of the carrier tape 170 through the opening, and based on these images, a cassette external motor may adjust the tape 170 for positioning a new lateral flow stick 180a, 180b, 180c, on which a new test is to be made, in relation to the needle 350.

The communication unit 230 may communicate via a wired or wireless communication interface, with a control unit 150, a database 140, and/or an output unit 160.

Such wireless communication interface may comprise, or at least be inspired by wireless communication technology such as Wi-Fi, 3GPP LTE, Bluetooth (BT) to name but a few possible examples of wireless communications in some embodiments.

The service module 120 may also comprise a first wireless communication device 240, configured for short distance wireless communication with a second wireless communication device 250 of the cassette 130. The short distance wireless communication may comprise Near Field Communication (NFC), Bluetooth (BT), Radio-Frequency Identification (RFID), Nano network, etc. By being able to communicate wirelessly, information may be exchanged between the service module 120 and the cassette 130. The control unit 150 may for example store certain data in a memory device 260 of the cassette 130.

The control unit 150 may comprise one or several processing circuitries, which may comprise one or more instances of e.g. a Central Processing Unit (CPU), a processor, a processing unit, an Application Specific Integrated Circuit (ASIC), a microprocessor, a Graphics Processing Unit (GPU), or other processing logic that may interpret and execute instructions. The herein utilised expression "processing circuitry" may thus represent a processing circuitry comprising a plurality of processing circuits, such as, e.g., any, some or all of the ones enumerated above.

The sensor 210 of the service module 120 is configured to inspect one lateral flow stick 180a, 180b, 180c on the tape 170 of the cassette 130, through the opening of the cassette 130. The sensor 210 may also assist in alignment of the needle 350 and the position of the lateral flow stick 180a, 180b, 180c on the tape 170, by adjusting the tape 170 by reels 131, 132 of the cassette 130.

Further, the service module 120 also comprises a tube element 220 configured to receive the milk sample of the animal 100 via a milking equipment and provide the milk sample to a needle 350, i.e. the needle 350 comprised in the dosing module.

The dosing module may in addition comprise at least one pump in some embodiments, configured to act on the tube element 220 for providing the milk sample to the needle 350. The pump may thus act on the tube element 220 to get the milk sample to propagate through the tube element 220, to reach the needle 350; or the mixing chamber 355 of the needle 350. The mixing chamber 355 may alternatively be external to the needle 350.

The dosing module may also comprise a liquid evacuator or drainage 195, which may collect liquid that has been output by the needle 350. The liquid, when comprising merely milk, may be returned back to the milk line in some embodiments. In other embodiments, when the milk has been mixed with diluent, the liquid may be conveyed away from the cassette 130 in order not to soak or contaminate other, unused, lateral flow sticks 180a, 180b, 180c of the tape 170 on the cassette 130.

The control unit 150 is configured to determine a biomarker value such as progesterone of the milk sample of the animal 100, based on an analysis of the image, captured by the sensor 210. The control unit 150 may be comprised in the service module 120 in some embodiments; or be external to the service module 120.

The database 140 may store measured biometric values of the animal 100, associated with an identity reference of the animal 100, a time stamp of the measurement and/or a reference colour tint of a control line of the lateral flow stick 180a, 180b, 180c. Other measurements and/or data related to the animal 100 may also be stored in the database 140, such as milk yield, e.g. measured by the milk flow meter, activity, breed, parity, rumination, lactation, resting, feed intake, energy balance, Days In Milk, milk production, age and possibly other similar animal status related parameters.

The output unit 160 may be e.g. a cellular mobile telephone, a stationary or portable computing device, a computer tablet, a display, a pair of intelligent glasses, a smart contact lens, an augmented reality device, a smart watch or similar device having a user interface and wireless communication ability.

Via the output unit 160, a farmer may take part of the result of the biomarker measurement of the milk sample. The farmer is thereby able to analyse the status of the animal 100, such as e.g. if/when the animal 100 is in heat, when progesterone level is measured.

When a deviation, exceeding a first threshold limit, is detected between the outcomes of the biomarker measurement and the corresponding reference value, an alert may be outputted to the farmer. The alert may comprise e.g. visual information, an audio message, a tactile signal or a combination thereof, encouraging the farmer to further investigate the reasons for the detected deviation in result. In case a plurality of people is working with the herd, a broadcast may be made to the plurality of farmers and their respective associated output units 160, in some embodiments.

FIG. 2B illustrates a tape 170 according to an embodiment. The cassette 130, which may be releasably inserted into the service module 120, comprises the tape 170, which in turn comprises a plurality of lateral flow sticks 180a, 180b, 180c.

The lateral flow sticks 180a, 180b, 180c may be arranged with an inclination a in relation to an axis 197, orthogonal to a longitudinal axis 196 of the tape 170. The inclination a may for example be 15 degrees or there about, or e.g. 10-30 degrees in some embodiments.

An opening 190a, 190b, 190c, may be arranged between at least some of the lateral flow sticks 180a, 180b, 180c, on the tape 170, or on a bottom film of the tape 170, i.e. between the welded seams 181a, 181b, 181c of at least some of the lateral flow sticks 180a, 180 b, 180c on the bottom film. The opening 190a, 190b, 190c is configured to convey liquid away from the lateral flow sticks 180a, 180b, 180c during cleaning, or before applying the milk sample to the lateral flow stick 180a, 180b, 180c.

Milk of a first animal 100 may contaminate a milk sample of another, subsequently tested animal. To avoid contamination, or carry over, the tubings and the needle 350 may be flushed with milk of the animal 100 to be tested before the milk sample is applied to the lateral flow stick 180a, 180b, 180c. For avoiding that the flushed milk of the animal 100 to be tested soaks and/or contaminate other unused lateral flow sticks 180a, 180b, 180c, the flushing may be made through the opening 190a, 190b, 190c of the tape 170, e.g. by lowering the needle 350 through the opening 190a, 190b, 190c, and capture the flushed milk with a liquid evacuator 195. The liquid evacuator 195 may then via a tube convey liquid away from the cassette 130.

The tape 170, or the bottom film of the tape 170 may further comprise a reference mark 185a, 185b, 185c, configured to assist a camera 210 in finding the lateral flow stick 180a, 180b, 180c. The reference mark 185a, 185b, 185c may comprise e.g. a hole, a colour mark, a barcode, a simple geometry, or similar.

The reference mark 185a, 185b, 185c may also assist the camera 210 in determining the advancement of the top film reel, to peel off the top film of the lateral flow stick 180a, 180b, 180c, enough to enable application of the milk sample to the lateral flow stick 180a, 180b, 180c, while not peeling off the top film of the next lateral flow stick 180a, 180b, 180c.

Further, the tape 170, or the bottom film of the tape 170 may comprise a first group 173 of advancement apertures 175, arranged at a first edge 171 of the tape 170; and a second group 174 of advancement apertures 175, arranged at a second edge 172 of the tape 170, or the bottom film of the tape 170.

Each lateral flow stick 180a, 180b, 180c may be separately arranged on the tape 170, or the bottom film of the tape 170, by a welded seam 181a, 181b, 181c, and wherein the sealed lateral flow sticks 180a, 180b, 180c are arranged on a distance from each other.

FIG. 3A and FIG. 3B illustrate a cross section of a lateral flow stick 180a, 180b, 180c in an embodiment. The lateral flow stick 180a, 180b, 180c is arranged to indicate at least one biomarker value of a milk sample of an animal 100 by a lateral flow test, which also may be referred to as a lateral flow immunochromatographic assay.

The lateral flow stick 180a, 180b, 180c comprises a sample pad 310, configured to receive the milk sample from the needle 350. Milk, or a liquid mix between milk and diluent may be applied on the sample pad 310. The sample pad 310 may comprise a porous structure for enabling capillary flow of the milk sample through the lateral flow stick 180a, 180b, 180c. The sample pad 310 may comprise or be made of cellulose fibres and/or woven meshes.

Further, the lateral flow stick 180a, 180b, 180c comprises a conjugate pad 315 comprising antibody treated gold particles, which are dispersed into the milk sample when the milk sample is absorbed from the sample pad 310.

The gold particles treated with antibodies will react with the progesterone in the applied milk sample. Typically, gold nanoparticles, coloured or fluorescent latex beads dried onto conjugate pads may be used as labelling agents, resulting in high levels of variation due to instability and inconsistent release, according to some embodiments.

The gold particles are embedded in the conjugate pad 315 which may comprise a glass fibre section at the upper part of the lateral flow stick 180a, 180b, 180c. Alternatively, the conjugate pad 315 may comprise cellulose and/or surface modified polyester. When the milk sample is supplied to the upper end of the lateral flow stick 180a, 180b, 180c, the milk will be drawn from the upper part to the lower part of the stick 180a, 180b, 180c with the aid of capillary forces.

The lateral flow stick 180a, 180b, 180c also comprises a porous membrane 320 for receiving a capillary flow of the milk sample, from the conjugate pad 315/sample pad 310.

The porous membrane 320 may comprise a nitrocellulose membrane, cellulose, glass fibre, polyester, rayon, a polymer, glass fibre, woven fibres, non-woven fibres, a chromatographic gel membrane, diatomaceous earth, silica gel, silicium oxide, kieselguhr, or other filtration membranes in different embodiments. The porous membrane 320 may be designed to enhance capillary pumping speed of liquid through the lateral flow stick 180a, 180b, 180c. The porous membrane 320 comprises a test line 360 and a control line 370.

The test line 360 is treated with a progesterone reference which binds the antibody treated gold particles of the milk sample and thereby brings the test line 360 to change colour tint when exposed for milk comprising a progesterone level lower than a threshold limit. Thus, the test line 360 changes colour tint into red/reddish when the milk has no or low progesterone level. If/when the animal 100 is in heat, the progesterone level is near zero in the milk sample. This colour change may then be detected by the sensor 210 and may be reported to the farmer and/or stored in a database 140 associated with an identity and/or a time reference of the animal 100. This may also trigger insemination of the animal 100.

The control line 370 of the porous membrane 320 is treated with an antibody reference which binds antibody treated gold particles of the milk sample regardless of the progesterone level in the milk, and thereby brings the control line 370 to change colour tint when exposed for milk comprising antibody treated gold particles.

Thereby, in case the antibody treated gold particles comprised in the conjugate pad 315 has reacted with heat, moisture, etc., due to inappropriate storage of the lateral flow stick 180a, 180b, 180c, the control line 370 will not change colour tint. The functionality of the lateral flow stick 180a, 180b, 180c may thereby be jeopardised, and as the lateral flow test is made autonomously, it is important to discover malfunctioning lateral flow sticks 180a, 180b, 180c and disregard any test made on them; and preferably replace them (or alert the farmer to replace them) with functional lateral flow sticks 180a, 180b, 180c before the next lateral flow test is performed.

At the bottom of the lateral flow stick 180a, 180b, 180c, an absorbent pad 330 may be arranged. The absorbent pad 330 may comprise an absorbent configured to absorb superfluous milk from the porous membrane 320. The absorbent pad 330 also may comprise a porous desiccant, configured to absorb moisture from environmental air.

Moisture in the air, during transportation or operation, may affect the outcome of the test of the biomarker, i.e. a different result than the true value may result from the test, leading to erroneous conclusions of the milk sample.

The biomarker value/progesterone level of the received milk sample may be determined by the sensor 210, such as a camera or video camera, taking an image of the test line 360, and the validity of the lateral flow test/lateral flow stick 180a, 180b, 180c may be determined by capturing an image of the control line 370 when the milk sample has been absorbed by the porous membrane 320. The control unit 150 may then obtain a reference colour tint of the control line 370 and compare it with the current colour tint of the control line 370, as determined by the sensor 210 and indicate validity of the lateral flow test on the lateral flow stick 180a, 180b, 180c, based on the made comparison.

In some embodiments, the lateral flow stick 180a, 180b, 180c may be individually sealed on the tape 170, by a welded seam 181a, 181b, 181c. Thereby, the lateral flow stick 180a, 180b, 180c may be protected from liquid and humidity, which may affect the biomarker measurement. However, in case the sealing breaks, the optional desiccant of the absorbent pad may serve the purpose of absorbing humidity from the environmental air. Thereby, a more reliable result of the biomarker measurement is achieved.

In some embodiments, the absorbent of the absorbent pad 330 may comprise cellulose fibres impregnated with the porous desiccant. The porous desiccant of the absorbent pad 330 may comprise e.g. silica gel, activated clay and/or molecular sieves.

The absorbent pad 330 may in some embodiments comprise a piece of paper having been treated with silica gel. Thereby, the desiccant paper of the absorbent pad 330 may offer high capacity adsorption within a semi-rigid structure. Millions of adsorbent particles may be comprised in a semi-rigid cellulose fibre matrix, which enables fast drying and extraordinary versatility in design.

Silica gel is an otherwise inert, nontoxic, water-insoluble white solid, which may be applied onto the absorbent pad 330. However, other alternative embodiments may comprise a desiccant comprising activated charcoal, calcium sulfate, calcium chloride, and molecular sieves such as e.g. zeolites.

Furthermore, the lateral flow stick 180a, 180b, 180c may comprise a carrying layer 340, upon which the sample pad 310, the porous membrane 320 and the absorbent pad 330 are arranged.

Further, the lateral flow stick 180a, 180b, 180c may be individually packaged on the carrying tape 170. The individually packaged lateral flow stick 180a, 180b, 180c may be sealed by a welded seam 181a, 181b, 181c, and wherein the sealed lateral flow stick 180a, 180b, 180c may be arranged at a distance from any other lateral flow stick 180a, 180b, 180c.

FIG. 4A illustrates a lateral flow stick 180a, 180b, 180c on which a lateral flow test has been performed. Both the test line 360 and the control line 370 have been changing colour into red/reddish.

The control unit 150 obtains a reference colour tint 380 of the control line 370, e.g. from a local memory 140, or a memory device of the cassette 130.

Thus, the control unit 150 determines a current colour tint of the control line 370, based on an image captured by the sensor 210 during the ongoing lateral flow test. The reference colour tint 380 is then compared with the current colour tint of the control line 370. The validity of the lateral flow test on the lateral flow stick 180a, 180b, 180c is then indicated, based on the made comparison.

In case the colour tint difference between the reference colour tint 380 and the current colour tint of the control line 370 exceeds a threshold limit, the lateral flow test is considered invalid. An alert may be generated in some embodiments, for alerting the farmer and encouraging him/her to change the lateral flow sticks 180a, 180b, 180c.

In the test result as illustrated in FIG. 4A, both the test line 360 and the control line 370 have changed colours into red. The colour tint difference between the reference colour tint 380 and the colour tint of the control line 370 is smaller than a threshold limit. Thereby, the lateral flow stick 180a, 180b, 180c is in appropriate condition and the lateral flow test is considered valid and reliable.

The control line 370 of the lateral flow stick 180a, 180b, 180c may be arranged more distant from the sample pad 310 than the test line 360 in some embodiments. It is thereby assured that, in case the control line 370 has changed colour, it means that there are sufficient gold particles that has passed the test line 360 of the porous membrane 320 to potentially change colour tint.

As the test line 360 also has changed colours into red, it indicates that the milk of the animal 100 comprises no or low progesterone level, i.e. a progesterone level lower than a threshold limit.

Low progesterone level (i.e. below the predetermined or configurable threshold limit) in the milk in turn indicates that the animal 100 is in heat, i.e. a stage of her oestrous cycle which is appropriate for insemination. By timing the insemination correctly, fertility at a herd level will increase and iteration of insemination could be avoided, which saves time for the farmer. Thus, an alert may be generated and sent to the farmer when the test line 360 has changed into red/colour, encouraging him/her to inseminate the particular animal 100.

For a cow, the oestrous cycle is approximately 21 days and the heat last for about 6-18 hours. By making the lateral flow test at each milking event of the animal 100 (the animal 100 is typically milked 2-4 times per day), chances are very good to detect each heat period of all the animals 100 at the farm. In some embodiments, by exploiting the knowledge that the oestrous cycle is about 21 days, the beginning of the (last) heat cycle of each animal 100 may be stored in the memory 140 associated with an identity reference of the animal 100, and the lateral flow test may be triggered after e.g. 20 days from the last detected heat of each particular animal 100 and iterated for a predetermined number of milking events until low progesterone is detected. In case the milk of the animal 100 has high progesterone at about 20-22 days from the last heat, the animal 100 is likely to be pregnant and it may be superfluous to make any more lateral flow tests on the animal 100 until after the calving. Thereby lateral flow sticks 180a, 180b, 180c are saved.

In the illustrated lateral flow stick 180a, 180b, 180c of FIG. 4B, the colour tint difference between the reference colour tint 380 and the colour tint of the control line 370 is smaller than a threshold limit. Thereby, the lateral flow stick 180a, 180b, 180c is in appropriate condition and the lateral flow test is considered valid and reliable.

However, the test line 360 has not changed any colours at all, indicating that the milk of the animal 100 is high on progesterone, i.e. higher than the threshold limit. There is no reason to attempt to inseminate the animal 100 as she will not be receptible for insemination.

In the illustrated lateral flow stick 180a, 180b, 180c of FIG. 4C, the test line 360 has not changed any colours at all, as on the lateral flow stick 180a, 180b, 180c of FIG. 4B. However, neither the control line 370 has changed colour tint, or not changed colour tint to a colour tint sufficiently similar/close to the reference colour tint 380. This may be discovered by comparing the reference colour tint 380 with the current colour tint of the control line 370.

The reference colour tint 380 of the control line 370 may be obtained by extraction of a prestored reference colour tint sample from a memory device 140, 260 in some embodiments.

In yet some embodiments, the reference colour tint 380 of the control line 370 may be obtained by extraction of a representation of a colour tint of the control line 370 of the lateral flow stick 180a, 180b, 180c, captured by the sensor 210 during a previous milk analysis session, from a memory device 140, 260. The reference colour tint 380 of the control line 370 may for example be determined and stored on the first, or one of the first lateral flow sticks 180a, 180b, 180c of a cassette 130 being used for the first time, or one of the first times.

The representation of the colour tint of the control line 370 may comprise for example a captured and stored image of the control line 370, a coordinate in the RGB colour space, a coordinate of a chromaticity space, a correlated colour temperature, hue, saturation, etc., stored in the memory device 140, 260.

By determining the reference colour tint 380 at an early stage of the usage of the cassette 130, it is assured that the chemicals of the lateral flow sticks 180a, 180b, 180c, have not been affected by high temperature, aging, increased humidity or other similar reason.

Thereby it may be indicated that the lateral flow test is invalid and cannot be trusted. An alert may be generated and sent to the farmer to encourage him/her to change the lateral flow stick 180a, 180b, 180c and/or to remake the lateral flow test.

Figure 4D:
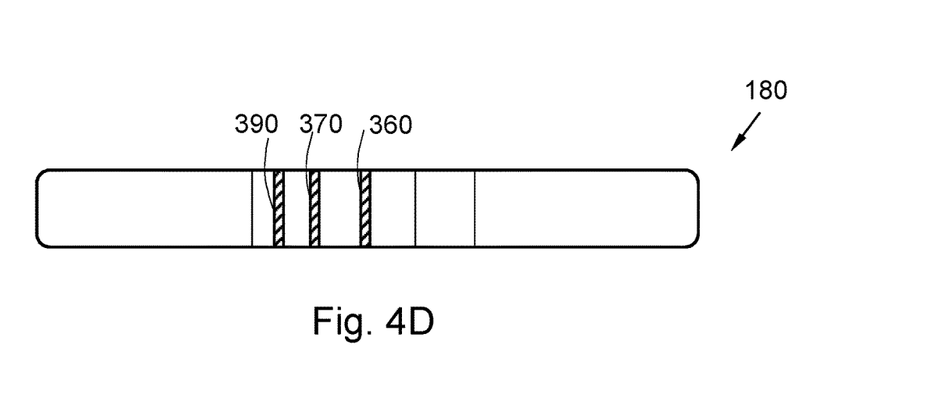
FIG. 4D illustrates a result of a lateral flow test on a lateral flow stick, according to an embodiment.

FIG. 4D illustrates a lateral flow stick 180a, 180b, 180c on which a lateral flow test has been performed. Both the test line 360 and the control line 370 have been changing colour into red/reddish.

In the illustrated embodiment, the lateral flow stick 180a, 180b, 180c comprises a reference line 390 comprising the reference colour tint 380. By applying the reference colour tint 380 physically onto the lateral flow stick 180a, 180b, 180c or the cassette 130 during the production process thereof.

The reference line 390 comprising the reference colour tint 380 may be treated with an antibody reference which binds antibody treated gold particles of the milk sample regardless of the progesterone level in the milk, similar to the control line 370. However, the reference line 390 may be sprayed or otherwise treated with gold particles at the manufacturing state of the lateral flow stick 180a, 180b, 180c. The reference line 390 thereby changes colour into the reference colour tint 380 and may be used as a reference indicator.

Thereby, the sensor 210 may capture an image of both the control line 370 and the reference colour tint 380 on the reference line 390 in one image. The reference line 390 may for example comprise a reference line parallel/adjacent to the control line 370 for a swift comparison between the colour tint of the control line 370 and the reference line 390.

An advantage with creating the reference line 390 comprising the reference colour tint 380 during the manufacturing is that the reference colour tint 380 is set at a point in time when it could be assured that the temperature conditions are controlled and ideal. Thereby, a reliable reference colour tint 380 is assured.

The control unit 150 may be configured to generate an alert when a colour tint difference exceeding a threshold limit is detected between the reference colour tint 380 of the control line 370 and the current colour tint of the control line 370.

The control unit 150 may in some embodiments be configured to disable usage of the lateral flow stick 180a, 180b, 180c comprising the control line 370, upon detection of the colour tint difference exceeding a threshold limit is detected between the reference colour tint 380 of the control line 370 and the current colour tint of the control line 370.

The system 10 may in some embodiments comprise a first wireless communication device 240. In at least some of those embodiments, the lateral flow stick 180a, 180b, 180c may be maintained in a cassette 130 comprising a second wireless communication device 250 for wireless communication with the first wireless communication device 240, and a memory device 260. The control unit 150 may then be configured to transmit a blocking sign prohibiting further usage of the cassette 130, via the first wireless communication device 240 and the second wireless communication device 250, for storage in the memory device 260 of the cassette 130, when the colour tint difference is detected.

The lateral flow stick 180a, 180b, 180c may be configured to expose at least a part of the control line 370 on the porous membrane 320 for direct visual contact with the sensor 210. The sensor 210, in turn, may be arranged to have direct visual contact with at least a part of the control line 370 on the porous membrane 320 of the lateral flow stick 180a, 180b, 180c when capturing the image thereof, in order to avoid optical distortion.

The tape 170 may comprise a bottom film 340, upon which lateral flow sticks 180a, 180b, 180c are separately arranged. The carrying tape 170 may comprise a top film configured to cover the lateral flow sticks 180a, 180b, 180c, arranged on the bottom film 340, and to be peeled off each individual lateral flow stick 180a, 180b, 180c before application of the milk sample to the lateral flow stick 180a, 180b, 180c.

The bottom film 340 of the carrying tape 170 may comprise a bottom layer, a medium layer and a top layer. The top film of the carrying tape 170 may comprise a bottom layer, a medium layer and a top layer. The bottom layer and the top layer of the bottom film 340 and/or the top film may be made of plastic while the medium layer may be made of aluminium, in some embodiments.

The aluminium foil may function as a moisture barrier, blocking liquid and moisture from reaching the lateral flow stick 180a, 180b, 180c, thereby keeping it dry and unaffected from being soaked.

The reason for applying the top film is that it is important that milk from a first animal 100 does not soak the lateral flow stick 180a, 180b, 180c on which a subsequent animal is to use for biomarker test, as the milk from the first animal 100 may contaminate the lateral flow stick 180a, 180b, 180c of the second animal. For this reason, besides assuring direct visual contact between the sensor 210 and the control line 370 on the porous membrane 320, the cassette 130 may further comprise a de-sealer, configured to remove the sealing tape from the lateral flow stick 180a, 180b, 180c when the lateral flow stick 180a, 180b, 180c is adjusted into a position aligned with the needle 350. The top film may be thinner than the bottom film 340 in some embodiments, such as e.g. 10% thinner, 20% thinner, 40% thinner, etc.

The bottom film 340 may comprise a bottom layer, a medium layer and a top layer. The bottom layer and the top layer may be made of plastic, like e.g. polyethylene, polypropylene, polyamide, polyethylene terephthalate, polyethylene terephthalate polyester, polychlorotrifluoro ethylene, polyvinylidene chloride, polypropylene, polyvinyl chloride and/or polystyrene or similar material such as a thermoplastic polyester. In particular, the top layer may be made of polyethylene.

The medium layer of the bottom film 340 may be made of aluminium or an aluminium based alloy, and e.g. have a thickness between 9 μm-25 μm.

The top film of the tape 170 may comprise a bottom layer, a medium layer and a top layer. The bottom layer and the top layer may be made of plastic, like e.g. polyethylene, polypropylene, polyimide, polyethylene terephthalate, polychlorotrifluoro ethylene, Polyvinylidene chloride, polypropylene, polyvinyl chloride and/or polystyrene or similar material. In particular, the bottom layer may with advantage be made of polyethylene.

The layers of the bottom film 340 and the layers of the top film, respectively, may be laminated.

The medium layer of the top film may be made of aluminium or an aluminium based alloy, and e.g. have a thickness between 9 μm-25 μm.

Using a thin layer of aluminium foil, e.g. around 9 μm, for medium layer of the bottom film 340 and/or the medium layer of the top film has the advantage of allowing more (longer) tape 170 on the spools 131, 132 of the cassette 130. It is also cheaper than using a thick (i.e. around 25 μm) aluminium foil. However, using a thicker aluminium foil for the medium layers makes the tape 170 less sensible to mechanical damage. A compromise may be to use a thick aluminium foil, such as about e.g. 15-25 μm for the medium layer of the bottom film 340 and a thinner aluminium foil (e.g. about 9-15 μm) for the medium layer of the top film, in some embodiments.

The lateral flow sticks 180a, 180b, 180c may be maintained between the bottom film 340 and the top film and be individually sealed. The individual sealing of each lateral flow stick 180a, 180b, 180c may be made by welding the top layer of the bottom film 340 together with the bottom layer of the top film. Thereby, the lateral flow sticks 180a, 180b, 180c are very well protected from milk stain, or humidity that may affect the operation of the lateral flow sticks 180a, 180b, 180c, when they are not in turn to receive the milk sample from the needle 350. In order to facilitate the welding, the top layer of the bottom film 340 and/or the bottom layer of the top film may be made of polyethylene, as polyethylene is easy to weld.

The purpose of the medium layers is to provide firmness to the tape 170, while yet allowing the tape 170 to be flexible enough to be rolled on the spools 131, 132 of the tape 170. For this purpose, the medium layers with advantage may be made of aluminium foil; or a foil made of an aluminium alloy. The aluminium foil of the medium layers creates a reliable moisture barrier, thereby assuring that the lateral flow sticks 180a, 180b, 180c are maintained in a dry state until the test is performed by application of the milk sample.

The purpose of the bottom layer of the bottom film 340 is to protect the medium layer from scratches and other undesired mechanical impact, as the medium layer, in particular when made of aluminium foil, is fragile and sensitive for scratches. The same may be said about the top layer of the top film. The bottom layer of the bottom film 340 and the top layer of the top film may with advantage be made of plastic as mentioned above. The plastic also has the advantage of low friction, which ascertain a smooth running of the tape 170 when being distributed between the spools 131, 132 of the tape 170. The plastic is also convenient to weld, so that each lateral flow stick 180a, 180b, 180c may be individually sealed.

At least some embodiments, or parts thereof, as illustrated in FIG. 1, FIG. 2A, FIG. 2B, FIG. 3A, FIG. 3B, FIG. 4A, FIG. 4B, FIG. 4C and/or FIG. 4D may with advantage be combined with each other for achieving further benefits.

The terminology used in the description of the embodiments as illustrated in the accompanying drawings is not intended to be limiting of the described lateral flow sticks 180a, 180b, 180c. Various changes, substitutions and/or alterations may be made, without departing from invention embodiments as defined by the appended claims.

As used herein, the term "and/or" comprises any and all combinations of one or more of the associated listed items. The term "or" as used herein, is to be interpreted as a mathematical OR, i.e., as an inclusive disjunction; not as a mathematical exclusive OR (XOR), unless expressly stated otherwise. In addition, the singular forms "a", "an" and "the" are to be interpreted as "at least one", thus also possibly comprising a plurality of entities of the same kind, unless expressly stated otherwise. It will be further understood that the terms "includes", "comprises", "including" and/or "comprising", specifies the presence of stated features, actions, integers, steps, operations, elements, and/or components, but do not preclude the presence or addition of one or more other features, actions, integers, steps, operations, elements, components, and/or groups thereof. A single unit such as e.g. a processor may fulfil the functions of several items recited in the claims. The mere fact that certain measures or features are recited in mutually different dependent claims, illustrated in different figures or discussed in conjunction with different embodiments does not indicate that a combination of these measures or features cannot be used to advantage. A computer program may be stored/distributed on a suitable medium, such as an optical storage medium or a solid-state medium supplied together with or as part of other hardware, but may also be distributed in other forms such as via Internet or other wired or wireless communication system.

The invention claimed is:

1. A system (10) for determining validity of a result of a lateral flow test, comprising:
   a lateral flow stick configured to indicate progesterone in a milk sample of an animal (100) by a lateral flow test, said lateral flow stick comprised of:
      a sample pad (310), configured to receive the milk sample,
      a conjugate pad (315) comprising antibody treated gold particles which disperse into the milk sample when the milk sample is absorbed from the sample pad (310), and
      a porous membrane (320) that receives a capillary flow of the milk sample from the conjugate pad (315), said porous membrane (320) comprising:
         a test line (360) treated with a progesterone reference which binds to said antibody treated gold particles of the milk sample and thereby causes the test line (360) to change colour tint when exposed to milk having a progesterone level lower than a threshold limit, and
         a control line (370) treated with an antibody reference which binds to said antibody treated gold particles of the milk sample regardless of the progesterone level of the milk and thereby causes the control line (370) to change colour tint when exposed to milk containing said antibody treated gold particles;
   a sensor (210) configured to capture an image of the control line (370) of the lateral flow stick when the milk sample has been absorbed by the porous membrane (320); and
   a control unit (150) configured to:
      obtain a reference colour tint (380) of the control line (370),
      determine a current colour tint of the control line (370), based on the image captured by the sensor (210) during the lateral flow test,
      carry out a comparison of the reference colour tint (380) of the control line (370) with the current colour tint of the control line (370), and
      indicate validity of the lateral flow test on the lateral flow stick, based on said comparison.

2. The system (10) according to claim 1, wherein the control unit (150) is further configured to generate an alert when a colour tint difference exceeding a threshold limit is detected between the reference colour tint (380) of the control line (370) and the current colour tint of the control line (370).

3. The system (10) according to claim 1, wherein the control unit (150) is configured to disable usage of the lateral flow stick upon detection of the colour tint difference exceeding a threshold limit between the reference colour tint (380) of the control line (370) and the current colour tint of the control line (370).

4. The system (10) according to claim 1, further comprising:
   a first wireless communication device (240); and
   a second wireless communication device (250),
   wherein the lateral flow stick is maintained in a cassette (130) comprised of a memory device (260) and said second wireless communication device (250) configured for wireless communication with the first wireless communication device (210), wherein the control unit (150) is configured to, when a colour tint difference exceeding a threshold limit is detected between the reference colour tint (380) of the control line (370) and the current colour tint of the control line (370):

transmit a blocking sign, to the second wireless communication device (250) via the first wireless communication device (240), for storage in the memory device (260) of the cassette (130) for prohibiting further usage of the cassette (130).

5. The system (10) according to claim 1, wherein the reference colour tint (380) of the control line (370) is obtained by extraction of a prestored reference colour tint sample from a memory device.

6. The system (10) according to claim 1, wherein the reference colour tint (380) of the control line (370) is obtained by extraction, from a memory device, of a representation of the control line (370) of the lateral flow stick captured by the sensor (210) during a previous milk analysis session.

7. The system (10) according to claim 1, wherein the reference colour tint (380) of the control line (370) is obtained by capturing an image of a reference line (390) of the lateral flow stick.

8. The system (10) according to claim 1, wherein the lateral flow stick is configured to expose at least a part of the control line (370) on the porous membrane (320) for direct visual contact with the sensor (210), and wherein the sensor (210) is arranged to have direct visual contact with at least a part of the control line (370) on the porous membrane (320) when capturing the image thereof, in order to avoid optical distortion.

9. The system (10) according to claim 1, wherein the control line (370) of the lateral flow stick is arranged more distant from the sample pad (310) than the test line (360).

* * * * *